US006887842B1

(12) United States Patent
Briesewitz et al.

(10) Patent No.: US 6,887,842 B1
(45) Date of Patent: May 3, 2005

(54) MODULATING A PHARMACOKINETIC PROPERTY OF A DRUG BY ADMINISTERING A BIFUNCTIONAL MOLECULE CONTAINING THE DRUG

(75) Inventors: Roger Briesewitz, Mountain View, CA (US); Gerald R. Crabtree, Woodside, CA (US); Thomas J. Wandless, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 337 days.

(21) Appl. No.: 09/716,841

(22) Filed: Nov. 17, 2000

Related U.S. Application Data
(60) Provisional application No. 60/166,633, filed on Nov. 19, 1999.

(51) Int. Cl.$^7$ .................. A61K 31/00; A61K 38/00; C12N 11/02; C07K 1/00; C07K 17/02

(52) U.S. Cl. .................. 514/1; 424/94.1; 424/94.5; 435/177; 514/2; 530/402; 530/812

(58) Field of Search .................. 514/1, 2; 424/94.1; 435/174, 177; 530/402, 810, 812

(56) References Cited

U.S. PATENT DOCUMENTS

| | | | |
|---|---|---|---|
| 5,382,657 A | 1/1995 | Karasiewicz et al. | 530/351 |
| 5,714,142 A | 2/1998 | Blaney et al. | 424/85.2 |
| 5,830,462 A | 11/1998 | Crabtree et al. | 424/93.21 |
| 5,834,266 A | 11/1998 | Crabtree et al. | 435/172.3 |
| 5,840,733 A | 11/1998 | Krantz et al. | 514/3.1 |
| 5,843,440 A | 12/1998 | Pouletty et al. | 422/33.1 |
| 5,869,337 A | 2/1999 | Crabtree et al. | 435/372.3 |
| 5,871,753 A | 2/1999 | Crabtree et al. | 424/280.1 |
| 6,372,712 B1 * | 4/2002 | Briesewitz et al. | 514/2 |
| 6,670,348 B1 | 12/2003 | Rosen et al. | 514/176 |
| 2002/0045570 A1 | 4/2002 | Rosen et al. | 514/2 |

FOREIGN PATENT DOCUMENTS

| | | |
|---|---|---|
| WO | WO 91/01743 | 2/1991 |
| WO | WO 94/18317 | 8/1994 |
| WO | WO 95/02684 | 1/1995 |
| WO | WO 95/05389 | 2/1995 |
| WO | WO 95/10302 | 4/1995 |
| WO | WO 96/06111 | 2/1996 |
| WO | WO 96/12796 | 5/1996 |
| WO | WO 96/13613 | 5/1996 |
| WO | WO 97/25074 | 7/1997 |
| WO | WO 97/29372 | 8/1997 |
| WO | WO 98/00171 | 1/1998 |
| WO | WO 98/11437 | 3/1998 |
| WO | WO 98/46270 | 10/1998 |
| WO | WO 98/47002 | 10/1998 |
| WO | WO 98/47916 | 10/1998 |

OTHER PUBLICATIONS

Kudak et al. "Synthesis and Evaluation of Geldanamycin–Testosterone Hybrids" *Bioorg—Med. Chem.. Lett.* 10 (2000) 1303–1306.

Srinivasa R. Karra et al. "99m Tc–Labeling and in Vivo Studies of a Bombesin Analogue with a Novel Water—Soluble Dithiadiphosphine–Based Bifunctional Chelating Agent" *Bioconjgate Chem.* 1999, 10, 254–260.

Snel C.A. Wilco et al. Database Biosis Online –Biosciences Information Service, Database Accession No. PREV199598364814 XP–002220714 "Disposition of the bromosulfophthalein–gluthatione conjugate in the isolated perfused rat kidney" (1995) Abstract *Journal of Pharmacology and Experimental Therapeutcs*, vol. 273, No. 3, 1995 (pp. 1300–1306, ISSN:0022–3565.

P.J. Hayball et al. Database Biosis Online –Biosciences Information Service, Database Accession No. 199294111953 XP002220709 "Stereoselective Interactions of Ketoprofen Glucuronides with Human Plasma Protein and Serum Albumin" Abstract *Biochemical Pharmacology*, vol. 44, No. 2. 1992 ppgs 291–299, ISSN:0006–2952.

I. Toth "A Novel Chemical Approach to Drug Delivery: Lipid Amino Acid Conjugates" *Journal of Drug Targeting*, Switzerland 1994, vol. 2, No. 3,pp. 217–239.

Al–Obeidi, et al., (1990) "Synthesis and Actions of a Melanotropin Conjugate, Ac–[Nle$^4$, Glu(gamma–4–'–hydroxyanilide)$^5$, D–Phe$^7$]α –MSH$_{4-10}$ – NH$_2$, on Melanocytes and Melanoma Cells In Vitro," *Journal of Pharmaceutical Sciences* vol. 79, No. (6):500–504.

Atwell, John L., et al., (1996) "Design and Expression of a Stable Bispecific scFv Dimer with Affinity for Both Glycophorin and N9 Neuraminidase," *Molecular Immunology* vol. 22, No. (17/18):1301–1312.

Belshaw, et al., (1996) "Controlling Protein Association and Subcellular Localization with a Synthetic Ligand that Induces Heterodimerization of Proteins," *Proc. Natl. Acad. Sci. U.S.A.* vol. 93:4604–4607.

Bernstein, Kenneth E., et al., (1990) "A Deeply Recessed Active Site in Angiotensin–Converting Enzyme Is Indicated From the Binding Characteristics of Biotin–Spacer–Inhibitor Reagents," *Biochemical and Biophysical Communications* vol. 167, No. (1):310–316.

(Continued)

*Primary Examiner*—David M. Naff
(74) *Attorney, Agent, or Firm*—Bret E. Field; Bozicevic, Field & Francis LLP

(57) ABSTRACT

Bifunctional molecules and methods for their use are provided. The subject bifunctional molecules are conjugates of a drug moiety and a pharmacokinetic modulating moiety, where these two moieties are optionally joined by a linking group. The bifunctional molecules are further characterized in that they exhibit at least one modulated pharmacokinetic property upon administration to a host as compared to a free drug control. The subject bifunctional molecules find use in a variety of therapeutic applications.

20 Claims, No Drawings

OTHER PUBLICATIONS

Bourdouxhe–Housiaux, Catherine, et al., (1996) "Interaction on DNA–Threading Peptide–Amsacrine Conjugates With DNA and Chromatin," *Anti–Cancer Drug Design* vol. 11:509–525.

Brochu, et al., (1992) "Modes of Action and Ihibitory Activities of New Siderophor–β–Lactam Conjugates that use Specific Iron Uptake Pathways for Entry into Bacteria," *Antimicrobial Agents and Chemotherapy* vol. 36, No. (10):2166–2175.

Briesewitz, et al., (1999) "Affinity Modulation of Small–Molecule Ligands by Borrowing Endogenous Protein Surfaces," *P.N.A.S* vol. 96, No. (5):1953–1958.

Chakraborty, TK., et al., (1995) "Design and Synthesis of a Rapamycin–Based High Affinity Binding FKBP12 Ligand," *Chemistry & Biology* vol. 2:157–161.

Crabtree, Gerald R., et al., (1996) "Three–Part Inventions: Intracellular Signalling and Induced Proximity," *Elsevier Trends Journal* pp:418–422.

Heath, et al., (1986) "Liposome–Mediated Delivery of Pteridine Antifolates to cells in Vitro: Potency of Methotrexate, and its α and γ Substituents," *Biochimica et Biophysica Acta* vol. 862:72–80.

Ho, Steffan N., et al., (1996) "Dimeric Ligands Define a Role for Transcriptional Activation Domains In Reinitiation," *Nature*, vol. 382, No. (6594):822–826.

Holt, et al., (1994) "Structure–Activity Studies of Synthetic FKBP Ligands as Peptidyl–Prolyl Isomerase Inhibitors," *Bioorganic and Medicinal Chemistry Letters* vol. 4, No. (2):315–320.

Kramer, Werner, et al., (1992) "Liver–Specific Drug Targeting by Coupling to Bile Acids," *The Journal of Biological Chemistry*, vol. 267, No. (2):18598–18604.

Luengo, et al., (1994) "Synthesis and Structure–Activity Relationships of Macrocyclic FKBP Ligands," *Bioorganic and Medicinal Chemistry Letters* vol. 4, No. (2):321–324.

Lussow, et al., (1996) "Targeting of Antihapten Antibodies to Activated T Cells via an IL–2–Hapten Conjugate Prolongs Cardiac Graft Survival," *Transplantation* vol. 62, No. (12):1703–1708.

Maeda, et al., (1997) "Amino Acids and Peptides XXXII: A Biofunctional Poly(Ethylene Glycol) Hybrid of Fibronectin–Related Peptides," *Biochemical and Biophysical Research Communications* vol. 241:595–598.

Mogre, R.M., et al., (1987) "A New Carbene Based Heterbifunctional Reagent: Photochemical Crosslinking of Aldolase," *FEBS Letters*, vol. 221, No. (2):408–414.

Mu, Yu., et al., (1999) "Bioconjugation of Laminin Peptide YIGSR With Poly(Styrene CO–Maleic Acid) Increases Its Antimetastaic Effect on Lung Metastasis of B16–BL6 Melanoma Cells," *Biochemical and Biophysical Research Communications*, vol. 255:75–79.

Varshavsky, Alexander, (1998) "Codominant Interference, Antieffectors, and Multitarget Drugs," *Proc. Natl. Acad. Sci. USA*, vol. 95:2094–2099.

Varshavsky, Alexander, (1995) "Codominance and Toxins: A Path to Drugs of Neatly Unlimited Selectivity," *Proc. Natl. Acad. Sci. USA*, vol. 92:3663–3667.

Zunino, et al., (1984) "Compassion of Antitumor Effects of Daunorubicin Covalently Linked to Poly–L–Amino Acid Carries," *Eur. J. Cancer Chem. Oncol.* vol. 20, No. (3):421–425.

Choi et al. (1996) "Structure of the FKBP12–Rapamycin Complex Interacting with the Binding Domain of Human FRAP." *Science*, vol. 273:239–242.

Clardy (1999) "Borrowing to make ends meet." *Proc. Natl. Acad. Sci. USA*, vol. 96:1826–1827.

Garboczi et al. (1996) "Structure of the complex between human T–cell receptor, viral peptide and HLA–A2." *Nature*, vol. 384:134–141.

Griffith et al. (1995) "X–Ray Structure of Calcineurin Inhibited by the Immunophilin–Immunosuppressant FKBP12–FK506 Complex." *Cell*, vol. 82:507–522.

Johnson et al. (1997) "Amino–terminal dimerization of an erythropoietin mimetic peptide results in increased erythropoietic activity." *Chemistry & Biology*, vol. 4:939–950.

Kissenger et al. (1995) "Crystal structures of human calcineurin and the human FKBP12–FK506–calcineurin complex." *Nature*, vol. 378:641–644.

Klemm et al. (1997) "Rapid targeting of nuclear proteins to the cytoplasm" *Current Biology*, vol. 7:638–644.

Livnah et al. (1996) "Functional Mimicry of a Protein Hormone by a Peptide Agonist: The EPO Receptor Complex at 2.8Å" *Science*, vol. 273;464–471.

Riviera et al. (1996) "A humanized system for pharmacologic control of gene expression." *Nature Medicine*, vol. 2(9):1028–1032.

Spencer et al. (1993) "Controlling Signal Transduction with Synthetic Ligands." *Science*, vol. 262:1019–1024.

Spencer et al. (1996) "Functional analysis of Fas signaling in vivo using synthetic inducers of dimerization." *Current Biology*, vol. 6(7):839–847.

\* cited by examiner

MODULATING A PHARMACOKINETIC PROPERTY OF A DRUG BY ADMINISTERING A BIFUNCTIONAL MOLECULE CONTAINING THE DRUG

CROSS REFERENCE TO RELATED APPLICATIONS

Pursuant to 35 U.S.C. § 119 (e), this application claims priority to the filing date of the U.S. Provisional Patent Application Ser. No. 60/166,633 filed Nov. 19, 1999, the disclosure of which is herein incorporated by reference.

ACKNOWLEDGMENT

This invention was made with United States Government support under Grant No. CA39612 awarded by National Institutes of Health. The United States Government has certain rights in this invention.

INTRODUCTION

1. Technical Field

The field of this invention is pharmacology.

2. Background of the Invention

Any chemical agent that affects any process of living is a drug. Drugs are a critical tool for health care practitioners, as they are used in the prevention, diagnosis and treatment of disease. Because of their criticality to the health care profession, annual world investment into the research and development of new chemical agents with therapeutic potential reaches into the billions of dollars. As a result, a large number of drugs have been developed to date and new chemical agents having potential therapeutic utility are frequently discovered. Chemical agents that find, or have found, use as drugs include naturally occurring and synthetic small molecules, as well as larger molecules, such as proteinaceous compounds.

A major challenge in the development of drugs is the predictable modulation of pharmacokinetic properties. Major pharmacokinetic parameters that effect the ability of a particular drug to treat a given condition include: the drug half-life, the hepatic first-pass metabolism of the drug, the volume of distribution of the drug, the degree of albumin binding of the drug, etc. Each of the above parameters can have a profound effect on the efficacy of a given drug agent.

As such, of great interest to the pharmaceutical industry and related fields would be the development of a methods for predictably modulating one or more of these pharmacokinetic properties so as to improve a given drug, e.g. the efficacy of a given drug. Of particular interest would be the development of a method which retained the small molecule nature of the drug, so as to retain the advantages of small molecule compounds with respect to drug delivery.

Relevant Literature

Patent publications of interest include: WO 91/01743; WO 94/18317; WO 95/02684; WO 95/10302; WO 96/06111; WO 96/12796; WO 96/13613; WO 97/25074; WO 97/29372; WO 98/11437; WO 98/47916; U.S. Pat. No. 5,714,142; U.S. Pat. No. 5,830,462; U.S. Pat. No. 5,843,440; and U.S. Pat. No. 5,871,753. References of interest include: Briesewitz et al., Proc. Nat'l Acad. Sci. USA (March 1999) 96: 1953–1958; Clardy, Proc. Nat'l Acad. Sci. USA (March 1999) 1826–1827; Crabtree & Schreiber, Elsevier Trends Journal (November 1996) 418–422; Spencer et al., Curr. Biol. (July 1996) 6:839–847; Spencer et al., Science (1993) 262: 1019; Chakraborty et al., Chem. & Biol. (March 1995) 2:157–161; Ho et al., Nature (1996) 382: 822; Riviera et al., Nature Medicine (1996) 2: 1028; Klemm et al., Current Biology (1997) 7: 638; Belshaw et al., Proc. Nat'l. Acad. Sci. USA (1996) 93: 4604; Livnah et al., Science (1996) 273: 464; Johnson et al., Chemistry and Biology, (1997) 4: 939; Garboczi et al., Nature (1996) 384:134; Kissenger et al., Nature (1995) 378:641; Griffith et al., Cell (1995) 82: 507; Choi et al., Science (1996) 273:239. Also of interest are Kramer et al., J. Biol. Chem. (1992) 267:18598–18604; and Varshavsky, Proc. Nat'l Acad. Sci. USA (March 1998) 95: 2094–2099; Varshavsky, Proc. Nat'l Acad. Sci. USA (April 1995) 92:3663–3667; and Mu et al., Biochem. Biophys. Res. Comm. (1999)255:75–79.

SUMMARY OF THE INVENTION

Bifunctional molecules and methods for their use are provided. The subject bifunctional molecules are conjugates of a drug moiety and a pharmacokinetic modulating moiety, where these two moieties are optionally joined by a linking group. The bifunctional molecules are further characterized in that they exhibit at least one modulated pharmacokinetic property upon administration to a host as compared to a free drug control. The subject bifunctional molecules find use in a variety of therapeutic applications.

DEFINITIONS

The term "bifunctional molecule" refers to a non-naturally occurring molecule that includes a pharmacokinetic modulating moiety and a drug moiety, where these two components may be covalently bonded to each other either directly or through a linking group.

The term "drug" refers to any active agent that affects any biological process. Active agents which are considered drugs for purposes of this application are agents that exhibit a pharmacological activity. Examples of drugs include active agents that are used in the prevention, diagnosis, alleviation, treatment or cure of a disease condition.

By "pharmacologic activity" is meant an activity that modulates or alters a biological process so as to result in a phenotypic change, e.g. cell death, cell proliferation etc.

By "pharmacokinetic property" is meant a parameter the describes the disposition of an active agent in an organism or host. Representative pharmacokinetic properties include: drug half-life, hepatic first-pass metabolism, volume of distribution, degree of blood serum protein, e.g. albumin, binding, etc.

By "half-life" is meant the time for one-half of an administered drug to be eliminated through biological processes, e.g. metabolism, excretion, etc.

By "hepatic first-pass metabolism" is meant the propensity of a drug to be metabolized upon first contact with the liver, i.e. during its first pass through the liver.

By "volume of distribution" is meant the distribution and degree of retention of a drug throughout the various compartments of an organisms, e.g. intracellular and extracellular spaces, tissues and organs, etc.

By "degree of blood serum binding" is meant the propensity of a drug to be bound by by a blood serum protein, such as albumin, in manner such that the activity of the drug is substantially dissipated if not abolished. This property is also referred to herein as the blood serum binding effect. In those embodiments where the blood serum protein is albumin, this property is also referred to as the albumin binding effect.

The term "efficacy" refers to the effectiveness of a particular active agent for its intended purpose, i.e. the ability of a given active agent to cause its desired pharmacologic effect.

DESCRIPTION OF THE SPECIFIC EMBODIMENTS

Bifunctional molecules and methods for their use are provided. The subject bifunctional molecules are conjugates of a drug moiety and a pharmacokinetic modulating moiety, where these two moieties are optionally joined by a linking group. The bifunctional molecules are further characterized in that they exhibit at least one modulated pharmacokinetic property upon administration to a host as compared to a free drug control. The subject bifunctional molecules find use in a variety of therapeutic applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Bifunctional Molecule

The bifunctional molecule of the subject invention is a non-naturally occurring or synthetic compound that is a conjugate of a drug or derivative thereof and a pharmacokinetic modulating moiety, where these two moieties are optionally joined by a linking group. The targeted bifunctional molecule is further characterized in that the pharmacokinetic modulating and drug moieties are different, such that the bifunctional molecule may be viewed as a heterodimeric compound produced by the joining of two different moieties. In many embodiments, the pharmacokinetic modulating moiety and the drug moiety are chosen such that the corresponding drug target and binding partner of the pharmacokinetic modulating moiety, e.g. corresponding pharmacokinetic modulating protein to which the pharmacokinetic modulating moiety binds, do not naturally associate with each other to produce a biological effect. As indicated above, the subject bifunctional molecules are small. As such, the molecular weight of the bifunctional molecule is generally at least about 100 D, usually at least about 400 D and more usually at least about 500 D, and may be as great as 2000 D or greater, but usually does not exceed about 5000 D.

The bifunctional molecule is further characterized in that it exhibits at least one modulated pharmacokinetic property, e.g. half-life, hepatic first-pass metabolism, volume of distribution, degree of albumin binding, etc., upon administration to a host as compared to free drug control. By modulated pharmacokinetic property is meant that the bifunctional molecule exhibits a change with respect to at least one pharmacokinetic property as compared to a free drug control. For example, a bifunctional molecule of the subject invention may exhibit a modulated, e.g. longer, half-life than its corresponding free drug control. Similarly, a bifunctional molecule may exhibit a reduced propensity to be eliminated or metabolized upon its first pass through the liver as compared to a free drug control. Likewise, a given bifunctional molecule may exhibit a different volume of distribution that its corresponding free drug control, e.g. a higher amount of the bifunctional molecule may be found in the intracellular space as compared to a corresponding free drug control. Analogously, a given bifunctional molecule may exhibit a modulated degree of albumin binding such that the drug moiety's activity is not as reduced, if at all, upon binding to albumin as compared to its corresponding free drug control. In evaluating whether a given bifunctional molecule has at least one modulated pharmacokinetic property, as described above, the pharmacokinetic parameter of interest is typically assessed at a time at least 1 week, usually at least 3 days and more usually at least 1 day following administration, but preferably within about 6 hours and more preferably within about 1 hour following administration.

Bifunctional molecules of the subject invention are generally described by the formula:

wherein:
  X is a drug moiety;
  L is bond or linking group; and
  Z is pharmacokinetic modulating moiety;
  with the proviso that X and Z are different.

Drug Moiety: X

The drug moiety X may be any molecule, as well as a binding portion or fragment, e.g. derivative, thereof, that is capable of modulating a biological process in a living host, either by itself or in the context of the pharmacokinetic modulating protein/bifunctional molecule binary complex. Generally, X is a small organic molecule that is capable of binding to the target of interest. As the drug moiety of the bifunctional molecule is a small molecule, it generally has a molecular weight of at least about 50 D, usually at least about 100 D, where the molecular weight may be as high as 500 D or higher, but will usually not exceed about 2000 D.

The drug moiety is capable of interacting with a target in the host into which the bifunctional molecule is administered during practice of the subject methods. The target may be a number of different types of naturally occurring structures, where targets of interest include both intracellular and extracellular targets, where such targets may be proteins, phospholipids, nucleic acids and the like, where proteins are of particular interest. Specific proteinaceous targets of interest include, without limitation, enzymes, e.g. kinases, phosphatases, reductases, cyclooxygenases, proteases and the like, targets comprising domains involved in protein—protein interactions, such as the SH2, SH3, PTB and PDZ domains, structural proteins, e.g. actin, tubulin, etc., membrane receptors, immunoglobulins, e.g. IgE, cell adhesion receptors, such as integrins, etc, ion channels, transmembrane pumps, transcription factors, signaling proteins, and the like.

The drug moiety of the bifunctional compound will include one or more functional groups necessary for structural interaction with the target, e.g. groups necessary for hydrophobic, hydrophilic, electrostatic or even covalent interactions, depending on the particular drug and its intended target. Where the target is a protein, the drug moiety will include functional groups necessary for structural interaction with proteins, such as hydrogen bonding, hydrophobic—hydrophobic interactions, electrostatic interactions, etc., and will typically include at least an amine, amide, sulfhydryl, carbonyl, hydroxyl or carboxyl group, preferably at least two of the functional chemical groups. As described in greater detail below, the drug moiety will also comprise a region that may be modified and/or participate in covalent linkage to the other components of the bifunctional molecule, such as the targeting moiety or linker, without substantially adversely affecting the moiety's ability to bind to its target.

The drug moieties often comprise cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The drug moiety of the bifunctional molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the drug moiety may be obtained from a library of naturally occurring or synthetic molecules, including a library of compounds produced through combinatorial means, i.e. a compound diversity combinatorial library. When obtained from such libraries, the drug moiety employed will have demonstrated some desirable activity in an appropriate screening assay for the activity. Combinatorial libraries, as well as methods for the production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Specific drugs of interest from which the drug moiety may be derived include, but are not limited to: psychopharmacological agents, such as (1) central nervous system depressants, e.g. general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g. analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g. anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g. central antitussives (opium alkaloids and their derivatives);

pharmacodynamic agents, such as (1) peripheral nervous system drugs, e.g. local anesthetics (ester derivatives, amide derivatives), (2) drugs acting at synaptic or neuroeffector junctional sites, e.g. cholinergic agents, cholinergic blocking agents, neuromuscular blocking agents, adrenergic agents, antiadrenergic agents, (3) smooth muscle active drugs, e.g. spasmolytics (anticholinergics, musculotropic spasmolytics), vasodilators, smooth muscle stimulants, (4) histamines and antihistamines, e.g. histamine and derivative thereof (betazole), antihistamines ($H_1$-antagonists, $H_2$-antagonists), histamine metabolism drugs, (5) cardiovascular drugs, e.g. cardiotonics (plant extracts, butenolides, pentadienolids, alkaloids from erythrophleum species, ionophores, -adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g. antianemia drugs, blood coagulation drugs (hemostatics, anticoagulants, antithrombotics, thrombolytics, blood proteins and their fractions), (7) gastrointestinal tract drugs, e.g. digestants (stomachics, choleretics), antiulcer drugs, antidiarrheal agents, (8) locally acting drugs;

chemotherapeutic agents, such as (1) anti-infective agents, e.g. ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e. antineoplastic agents or cytotoxic drugs, such as alkylating agents, e.g. Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g. Vincristine (Oncovin), Vinblastine (Velban, Velbe), Paclitaxel (Taxol), and the like; antimetabolites, e.g. Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g. Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g. Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16–213), Amsarcrine (AMSA, m-AMSA), Mitotane (Lysodren), Mitoxantrone (Novatrone), and the like;

Antibiotics, such as: aminoglycosides, e.g. amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g. azidamfenicol, chloramphenicol, florfenicol, and theimaphenicol; ansamycins, e.g. rifamide, rifampin, rifamycin, rifapentine, rifaximin; β-lactams, e.g. carbacephems, carbapenems, cephalosporins, cehpamycins, monobactams, oxaphems, penicillins; lincosamides, e.g. clinamycin, lincomycin; macrolides, e.g. clarithromycin, dirthromycin, erythromycin, etc.; polypeptides, e.g. amphomycin, bacitracin, capreomycin, etc.; tetracyclines, e.g. apicycline, chlortetracycline, clomocycline, etc.; synthetic antibacterial agents, such as 2,4-diaminopyrimidines, nitrofurans, quinolones and analogs thereof, sulfonamides, sulfones;

Antifungal agents, such as: polyenes, e.g. amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g. butenafine, naftifine, terbinafine; imidazoles, e.g. bifonazole, butoconazole, chlordantoin, chlormidazole, etc., thiocarbamates, e.g. tolciclate, triazoles, e.g. fluconazole, itraconazole, terconazole;

Anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

Antiprotozoan agents, such as: acranil, tinidazole, ipronidazole, ethylstibamine, pentamidine, acetarsone, aminitrozole, anisomycin, nifuratel, tinidazole, benzidazole, suramin, and the like.

Name brand drugs of interest include, but are not limited to: Rezulin™, Lovastatin™, Enalapril™, Prozac™, Prilosec™, Lipotor™, Claritin™, Zocor™, Ciprofloxacin™, Viagra™, Crixivan™, Ritalin™, and the like.

Drug compounds of interest from which drug moieties may be derived are also listed in: Goodman & Gilman's, The Pharmacological Basis of Therapeutics (9th Ed) (Goodman et al. eds) (McGraw-Hill) (1996); and 1999 Physician's Desk Reference (1998).

Specific compounds of interest also include, but are not limited to:

antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 476,925, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psycopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620, 5,665,752, 5,656,661, 5,635,516, 5,631,283, 5,622,948, 5,618,835, 5,607,959, 5,593,980, 5,593,960, 5,580,888, 5,552,424, 5,552,422, 5,516,764, 5,510,361, 5,508,026, 5,500,417, 5,498,405, 5,494,927, 5,476,876, 5,472,973, 5,470,885, 5,470,842, 5,464,856, 5,464,849, 5,462,952, 5,459,151, 5,451,686, 5,444,043, 5,436,265, 5,432,181, RE034918, U.S. Pat. Nos. 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 500,654, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

analgesic agents, as disclosed in U.S. Pat. Nos. 5,292,736, 5,688,825, 5,554,789, 5,455,230, 5,292,736, 5,298, 522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents, as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874,479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102;

the disclosures of which are herein incorporated by reference.

The drug moiety of the bifunctional molecule may be the whole compound or a derivative thereof, e.g. a binding fragment or portion thereof, that retains its affinity and specificity for the target of interest, and therefor its desired activity, while having a linkage site for covalent bonding to the targeting moiety or linker.

Pharmacokinetic Modulating Moiety: Z

Z is a pharmacokinetic modulating moiety that is a ligand for a biological entity endogenous to the host to which the bifunctional molecule is administered, where binding of the modulating moiety to this biological entity results in modulation of at least one pharmacokinetic property of the drug moiety of the bifunctional molecule, as compared to the drug moiety's corresponding free drug control. In many embodiments, this biological entity to which the modulating moiety of the bifunctional molecule binds is a protein, e.g. an intracellular or extracellular protein. As such, in many embodiments this biological entity is properly referred to the endogenous pharmacokinetic modulating protein.

The binding interaction between the modulating moiety of the bifunctional molecule and the endogenous biological entity, e.g. endogenous pharmacokinetic modulating protein, is non-covalent, such that no covalent bonds are produced between the bifunctional molecule and the pharmacokinetic modulating protein upon binding of the two entities. As the pharmacokinetic modulating moiety of the bifunctional molecule is a small molecule, it generally has a molecular weight of at least about 50 D, usually at least about 100 D, where the molecular weight may be as high as 500 D or higher, but will usually not exceed about 2000 D. In certain embodiments, the pharmacokinetic modulating moiety, in the context of the bifunctional molecule, has substantially no pharmacological activity at its effective concentration beyond binding to its corresponding endogenous pharmacokinetic modulating protein, i.e. it does not directly cause a pharmacokinetic modulating protein-mediated pharmacological event to occur upon binding at its effective concentration to the pharmacokinetic modulating protein, where a pharmacokinetic modulating protein mediated pharmacological event is a pharmacologically relevant event which is directly modulated by the pharmacokinetic modulating protein in the absence of the subject bifunctional molecules. In other certain embodiments, the modulating moiety may have some pharmacological activity, where this pharmacological activity does not adversely effect the host to the extent that the therapy in which the bifunctional molecule is employed places the host in a worst condition than prior to the therapy. In other words, pharmacological activity in the modulating moiety may be tolerated in these embodiments to the extent that any consequences of such activity, if any, are outweighed by the benefits provided by the bifunctional molecule. As used herein, pharmacological event is an event that is distinct from a biochemical event (e.g. inhibition a prolyl isomerase activity) or a biological event (e.g. inducement of a cell to express new genes).

The pharmacokinetic modulating protein to which the modulating moiety of the bifunctional molecule binds may be any protein that is present in the host at the time the bifunctional molecule is introduced to the host, i.e. the pharmacokinetic modulating protein is one that is endogenous to the host. The pharmacokinetic modulating protein may or may not have one or more modified residues, e.g. residues that are glycosylated, such that it may or may not be a glycoprotein. Furthermore, the pharmacokinetic modulating protein to which the bifunctional molecule binds via the pharmacokinetic modulating moiety may or may not be part of a complex or structure of a plurality of biological molecules, e.g. lipids, where such complexes or structures may include lipoproteins, lipid bilayers, and the like. However, in many embodiments, the pharmacokinetic modulating protein to which the bifunctional molecule binds will be by itself, i.e. will not be part of a larger structure of a plurality of biological molecules. Though the pharmacokinetic modulating protein may be a protein that is not native to the host but has been introduced at some time prior to introduction of the bifunctional molecule, e.g. through prior administration of the protein or a nucleic acid composition encoding the same, such as through gene therapy, the pharmacokinetic modulating protein will, in many embodiments, be a protein that is native to and naturally expressed by at least some of the host's cells, i.e. a naturally occurring protein in the host. The pharmacokinetic modulating protein is a protein that is present in the region of host occupied by the drug target. As such, where the drug target is an intracellular drug target, the pharmacokinetic protein will be an intracellular protein present in the cell comprising the target, typically expressed in the cell comprising the target, i.e. the pharmacokinetic modulating protein and target are co-expressed in the same cell. Likewise, where the drug target is an extracellular drug target, the pharmacokinetic modulating protein will be an extracellular protein that is found in the vicinity of the target.

Although not a requirement in certain embodiments, in many preferred embodiments the pharmacokinetic modulating protein is one that is present in the host in sufficient quantities such that, upon binding of at least a portion of pharmacokinetic modulating protein present in the host to the bifunctional molecule, adverse pharmacological effects do not occur. In other words, the pharmacokinetic modulating protein in these preferred embodiments is one in which its native and desirable biological activity, if any, is not diminished by an unacceptable amount following binding of the portion of the pharmacokinetic modulating protein population to the bifunctional molecule. The amount of diminished activity of the pharmacokinetic modulating protein that is acceptable in a given situation is determined with respect to the condition being treated in view of the benefits of treatment versus the reduction of overall pharmacokinetic modulating protein activity, if any. In certain situations, a large decrease in overall pharmacokinetic modulating protein activity may be acceptable, e.g. where the pharmacokinetic modulating protein activity aggravates the condition being treated.

The specific pharmacokinetic modulating protein to which the modulating moiety of the subject bifunctional molecule binds may vary greatly depending on the desired modulation of the one or more pharmacokinetic properties or parameters of interest. For example, where one wishes to modulated the half-life, hepatic first-pass metabolism, or volume of distribution, intracellular proteins are often of interest, where representative intracellular proteins of interest include: peptidyl-prolyl isomerases, e.g. FKBPs and cyclophilins; ubiquitously expressed molecular chaperones, e.g. Heat Shock Protein 90 (Hsp90); steroid hormone receptors, e.g. estrogen receptors, glucocorticoid receptors, androgen receptors; retinoic acid binding protein, cytoskeletal proteins, such as tubulin and actin; etc. Of particular interest as intracellular pharmacokinetic modulating proteins are cis-trans peptidyl-prolyl isomerases which interact with many proteins because of their chaperonin/isomerase activity, e.g. FKBPs and cyclophilins. Peptidyl-prolyl isomerases of interest include FKBPs. A number of different FKBPs are known in the art, and include those described in: Sabatini et al., Mol. Neurobiol. (October 1997) 15:223–239; Marks, Physiol. Rev. (July 1996) 76:631–649; Kay, Biochem J. (March, 1996)314: 361–385; Braun et al., FASEB J. (January 1995)9:63–72; Fruman et al, FASEB J. (April 1994) 8:391–400; and Hacker et al., Mol. Microbiol. (November 1993) 10: 445–456. FKBPs of interest include FKBP 12, FKBP 52, FKBP 14.6 (described in U.S. Pat. No. 5,525,523, the disclosure of which is herein incorporated by reference); FKBP 12.6 (described in U.S. Pat. No. 5,457,182 the disclosure of which is herein incorporated by reference); FKBP 13 (described in U.S. Pat. No. 5,498,597, the disclosure of which is herein incorporated by reference); and HCB (described in U.S. Pat. No. 5,196,352 the disclosure of which is herein incorporated by reference); where FKBP 12 and FKBP 52 are of particular interest as intracellular pharmacokinetic modulating proteins. Also of specific interest as intracellular pharmacokinetic modulating proteins are cyclophilins. A number of cyclophilins are known in the art and are described in Trandinh et al., FASEB J. (December 1992)6: 3410–3420; Harding et al., Transplantation (August 1988) 46: 29S–35S. Specific cyclophilins of interest as intracellular pharmacokinetic modulating proteins include cyclophilin A, B, C, D, E, and the like, where cyclophilin A is of particular interest.

Instead of being an intracellular protein, in certain embodiments the endogenous pharmacokinetic modulating protein is an extracellular or serum protein, e.g. where extracellular pharmacokinetic modulating proteins find use in the modulating of half-life, volume of distribution, and degree of albumin binding or albumin binding effect. Serum pharmacokinetic modulating proteins of particular interest are those that are relatively abundant in the serum of the host and meet the above criteria for suitable endogenous pharmacokinetic modulating proteins. By relatively abundant is meant that the concentration of the serum pharmacokinetic modulating protein is at least about 1 ng/ml, usually at least about 10 $\mu$g/ml and more usually at least about 15 $\mu$g/ml. Specific serum proteins of interest as pharmacokinetic modulating proteins include: albumin, Vitamin A binding proteins and Vitamin D binding proteins, $\beta$-2 macroglobulin, $\alpha$-1 acid glycoprotein, with albumin being a particularly preferred pharmacokinetic modulating protein in many embodiments.

The Z moiety of the subject bifunctional molecules will therefore be chosen; in view of the endogenous pharmacokinetic modulating protein that is to be used to bind to the bifunctional molecule and thereby achieve the desired pharmacokinetic property modulation. As such, the Z moiety may be a number of different ligands, depending on the particular endogenous pharmacokinetic modulating protein to which it is intended to bind. In many preferred embodiments, the Z moiety has an affinity for its pharmacokinetic modulating protein of at least about $10^{-4}$ M, usually at least about $10^{-6}$ molar and more usually at least about $10^{-8}$ M, where in many embodiments the Z moiety has an affinity for its pharmacokinetic modulating protein of between about $10^{-9}$ and $10^{-12}$ M. The Z moiety portion of the bifunctional molecule should also be specific for the pharmacokinetic modulating protein in the context of its binding activity when present in the bifunctional molecule, in that it does not significantly bind or substantially affect non-pharmacokinetic modulating proteins when it is present in the bifunctional molecule.

Representative ligands capable of serving as the Z moiety of the bifunctional molecule include ligands for intracellular proteins, such as: peptidyl-prolyl isomerase ligands, e.g. FK506, rapamycin, cyclosporin A and the like; Hsp90 ligands, e.g. geldanamycin; steroid hormone receptor ligands, e.g. naturally occurring steroid hormones, such as estrogen, progestin, testosterone, and the like, as well as synthetic derivatives and mimetics thereof, particularly those which bind with high specificity and affinity but do not activate their respective receptors; small molecules that bind to cytoskeletal proteins, e.g. antimitotic agents, such as taxanes, colchicine, colcemid, nocadozole, vinblastine, and vincristine, actin binding agents, such as cytochalasin, latrunculin, phalloidin, and the like.

As mentioned above, in certain preferred embodiments the intracellular pharmacokinetic modulating proteins are members of the peptidyl-prolyl isomerase family, particularly the FKBP and cyclophilin subsets of this family. Where peptidyl-prolyl isomerase pharmacokinetic modulating proteins are employed, the bifunctional molecule/peptidyl-prolyl isomerase complex will preferably not substantially bind to the natural peptidyl-prolyl isomerase/ligand target calcineurin so as to result in significant immunosuppression. A variety of ligands are known that bind to FKBPs and may be used in the subject invention. The ligands should specifically bind to an FKBP and have an affinity for the FKBP that is between about $10^{-6}$ and $10^{-10}$ M. Of interest are both naturally occurring FKBP ligands, including FK506 and rapamycin. Also of interest are synthetic FKBP ligands, including those described in U.S. Pat. Nos. 5,665,774; 5,622,970; 5,516,797; 5,614,547; and 5,403,833, the disclosures of which are herein incorporated by reference.

Also of interest in this particular set of preferred embodiments are cyclophilin ligands, where such ligands should specifically bind to cyclophilin with an affinity that is between about $10^{-6}$ and $10^{-9}$ M. A variety of ligands that bind to cyclophilins are also known, where such ligands include the naturally occurring cyclosporins, such as cyclosporin A, as well as synthetic derivatives and mimetics thereof, including those described in U.S. Pat. Nos. 5,401,649; 5,318,901; 5,236,899; 5,227,467; 5,214,130; 5,122,511; 5,116,816; 5,089,390; 5,079,341; 5,017,597; 4,940,719; 4,914,188; 4,885,276; 4,798,823; 4,771,122; 4,703,033; 4,554,351; 4,396,542; 4,289,851; 4,288,431; 4,220,61 and 4,210,581, the disclosures of which are herein incorporated by reference.

Representative ligands for use as the Z moiety in the bifunctional molecule also include ligands that bind to extracellular pharmacokinetic modulating proteins. Such ligands should specifically bind to their respective extracellular pharmacokinetic modulating protein with an affinity of at least about $10^{-4}$ M. Ligands of interest for use in binding to extracellular pharmacokinetic modulating proteins include: albumin ligands, such as arachidonate, bilirubin, hemin, aspirin, ibuprofen, para-amino salicylic acid, myristylate, plamitate, linoleate, warfarin, sulfisoxazole, chlorpromazine, etc.; α-1 acid glycoprotein ligands, e.g. small neutral or basic molecules, e.g. propanolol, chlorpromazine, dipyrimadole, metoclopramide, aprindine, verapamil, and the like; Vitamin A and derivatives thereof, Vitamin D and derivatives thereof, and the like.

Linking Moiety: L

The Z and X moieties of the bifunctional molecule are joined together through linking moiety L, where L may be either a bond or a linking group. Where linking groups are employed, such groups are chosen to provide for covalent attachment of the drug and ligand moieties through the linking group, as well as the desired structural relationship of the bifunctional molecule with respect to its intended pharmacokinetic modulating protein. Linking groups of interest may vary widely depending on the nature of the drug and ligand moieties. The linking group, when present, should preferably be biologically inert. Appropriate linkers can readily be identified using the affinity, specificity or selectivity assays described supra. A variety of linking groups are known to those of skill in the art and find use in the subject bifunctional molecules. The linker groups should be sufficiently small so as to provide a bifunctional molecule having the overall size characteristics as described above, the size of the linker group, when present, is generally at least about 50 daltons, usually at least about 100 daltons and may be as large as 1000 daltons or larger, but generally will not exceed about 500 daltons and usually will not exceed about 300 daltons. Generally, such linkers will comprise a spacer group terminated at either end with a reactive functionality capable of covalently bonding to the drug or ligand moieties. Spacer groups of interest include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linker groups that may find use in the subject bifunctional molecules include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobertzoate, N-succinimidyl[4-azidophenyl]-1,3'-dithiopropionate, N-succinimidyl[4-iodoacetyl]aminobenzoate, glutaraldehyde, and succinimidyl 4-[N-maleimidomethyl]

cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

Methods of Making Bifunctional Molecules

The bifunctional molecules of the subject invention may be prepared using any convenient methodology. In many embodiments of the subject invention, the invention is used to modulate the pharmacokinetic properties of an identified and at least partially characterized small molecule drug. Generally, a small molecule drug of interest is first identified. The drug may be a previously identified biologically active agent or compound having the desired target binding activity, or one that has been newly discovered using one or more drug discovery techniques. The bifunctional molecule is then generally produced from the drug using a rational or combinatorial approach.

In a rational approach, the bifunctional molecules are constructed from their individual components, e.g. pharmacokinetic modulating moiety, linker and drug. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used in covalently bonding the components together to produce the bifunctional molecule include: hydroxy, sulfhydryl, amino, and the like. The particular portion of the different components that are modified to provide for covalent linkage will be chosen so as not to substantially adversely interfere with that components desired binding activity, e.g. for the drug moiety, a region that does not affect the target binding activity will be modified, such that a sufficient amount of the desired drug activity is preserved. Where necessary and/or desired, certain moieties on the components may be protected using blocking groups, as is known in the art, see, e.g. Green & Wuts, Protective Groups in Organic Synthesis (John Wiley & Sons) (1991).

The above component approach to production of the bifunctional molecule is best suited for situations where the crystal structures of the pharmacokinetic modulating protein, the pharmacokinetic modulating moiety, the drug and the target are known, such that molecular modeling can be used to determine the optimal linker size, if any, to be employed to join the different components.

Alternatively, the bifunctional molecule can be produced using combinatorial methods to produce large libraries of potential bifunctional molecules which may then be screened for identification of a bifunctional, molecule with the pharmacokinetic profile. Methods for producing and screening combinatorial libraries of molecules include: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Alternatively, the bifunctional molecule may be produced using medicinal chemistry and known structure-activity relationships for the targeting moiety and the drug. In particular, this approach will provide insight as to where to join the two moieties to the linker.

Methods for Making Bifunctional Molecules for Peptidyl-Prolyl Isomerase Pharmacokinetic Modulating Proteins As mentioned above, one class of preferred embodiments of the subject invention are those embodiments in which the bifunctional molecules comprise a pharmacokinetic modulating moiety that binds to an intracellular protein. In these embodiments, of particular interest are those bifunctional molecules in which the pharmacokinetic modulating moiety specifically binds to endogenous peptidyl-prolyl isomerase pharmacokinetic modulating proteins present in the host into which the bifunctional molecule is introduced. Thus, bifunctional molecules of interest include those in which the endogenous pharmacokinetic modulating protein is either an FKBP or a cyclophilin.

In preparing bifunctional molecules from FK506, a suitable attachment site on the FK506 structure is identified, modified as necessary, and then covalently attached to the linker or drug moiety. The structure of FK506 (also known as tacrolimus) is:

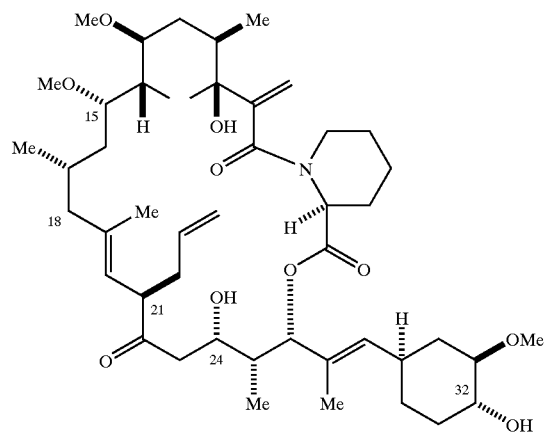

The site to which the linker/drug moiety is covalently attached is one that, upon covalent attachment, does not ablate the affinity and/or specificity of FK506 for its FKBP pharmacokinetic modulating protein, e.g. FKBP 12 or FKBP 52. As such, positions suitable for use as covalent linkage sites include atoms located between carbon 15 and carbon 25 and the substituents attached to these atoms. For example, oxidation of the allyl group or oxidation of the carbon 18 methylene group; modification of the carbon 22 ketone or the carbon 24 hydroxyl group or alkylation at carbon 21 or carbon 23; as well as the secondary hydroxyl group located on the cyclohexyl ring (carbon 32); are potential specific covalent linkage sites.

With FK506, depending on the drug moiety and/or linker to be attached, it may be desirable to introduce one or more functional moieties onto the FK506 structure. Functional moieties of interest that may be introduced include: hydroxyl groups, amino groups, carboxyl groups, aldehydes, carbonates, carbamates, azides, thiols, and esters, etc. Such groups may be introduced using known protocols, such as oxidation reactions, reduction reactions, cleavage reactions and the like, with or without the use of one or more blocking groups to prevent unwanted side reactions.

In some instances, it is desirable to covalently attach the drug moiety directly to FK506, often activated FK506. In such instances, the reactive functional group(s) introduced onto the FK506 structure will depend primarily on the nature of the drug moiety to be attached. Thus, for peptidic drug moieties, specific pairings of interest include: FK506 carbonates for reacting with amino groups of peptides; FK506 carboxylic acids for reacting with amino groups of peptides; FK506 amines for reacting with carboxylic acid groups of peptides; FK506 maleimide for reacting with thiol groups of peptides; and the like. Alternatively, where the drug moiety is a steroid, potential pairings of interest include: FK506 N-hydroxysuccinimidyl carbonate and partner amine; FK506 aldehyde and partner amine; FK506 aldehyde and partner hydrazide; FK506 hydroxy group and partner carboxylic acid OR alkyl halide; FK506 thiol and partner maleimide and the like.

Following introduction of the reactive functional group(s) onto the FK506 structure, the activated FK506 is then combined with the drug moiety/linker under conditions sufficient for covalent bonding to occur.

Another embodiment of particular interest are bifunctional molecules of cyclosporin A or analogs thereof. The structure of cyclosporin A is:

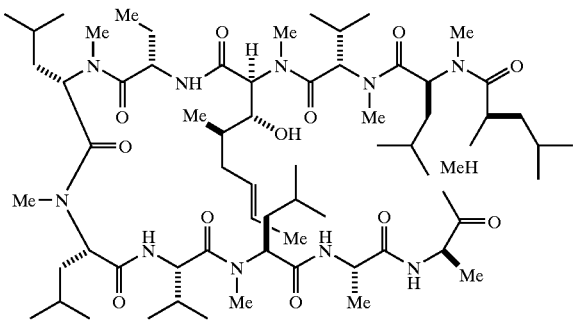

As with the FK506 bifunctional molecules, the cyclosporin A will be conjugated to the drug moiety in a manner such that cyclosporin A does not substantially lose its affinity for cyclophilin. Preferred positions on the cyclosporin A structure that may serve as covalent linkage sites include: residues 4, 5, 6, 7, 8; while less preferred but still possible residues include: 1, 2, 3, 9, 10 and 11. Where necessary, reactive functionalities may be introduced onto the cyclosporin structure, where such functionalities include: hydroxyl groups, amino groups, carboxyl groups, aldehydes, carbonates, carbamates, azides, thiols, and esters, etc., with the particular functionality of interest being chosen with respect to the specific linker or drug moiety to be attached.

Screening Bifunctional Compounds

The resultant bifunctional molecules are then screened for those molecules that exhibit the desired pharmacokinetic profile, e.g. desired half-life, desired hepatic first-pass metabolism, desired volume of distribution and/or desired degree of albumin binding. Any convenient screening assay may be employed, where the particular screening assay may be one known to those of skill in the art or one developed in view of the specific molecule and property being studied. Suitable screening assays for identifying those bifunctional molecules that exhibit at least a modulated pharmacokinetic property as compared to a free drug control, e.g. for evaluating drug half-life, volume of distribution, first-pass metabolism and degree of albumin binding, are known to those of skill in the art and need not be described further here.

Specific Improvements as Compared to Free Drug

As mentioned above, the bifunctional molecules of the subject invention exhibit at least one modulated pharmacokinetic property upon administration of to a host as compared to their corresponding free drug, i.e. a free drug control. In other words, at least one of the pharmacokinetic properties of the subject bifunctional molecules differ from that of the corresponding free drug. Specific pharmacokinetic properties that may differ in the subject bifunctional molecules are drug half-life, drug first-pass metabolism, drug volume of distribution and degree of drug binding to a serum protein, e.g. albumin. In certain embodiments, the above improvements are achieved through the formation of binary or tripartite complexes, as described in application Ser. No. 09/316,932 entitled Bifunctional Molecules and Therapies Based Thereon, the disclosure of which is herein incorporated by reference.

In those embodiments where the half-life of a drug is modulated, e.g. prolonged, by incorporating it into a bifunctional molecule, the modulating moiety of the bifunctional molecule may be a ligand for an intracellular or extracellular protein, as described above. In these embodiments, the modulating moiety is a ligand for an intracellular or extracellular protein that will serve to, when bound to the bifunctional molecule, i.e. when present as a binary complex with the bifunctional molecule, protect or shield the drug moiety from biotransformation or excretion, e.g. by the liver or the kidney. These intracellular pharmacokinetic modulating proteins are generally proteins that are highly abundant in cells and thus the intracellular space of the host, e.g. the interior or erythrocytes, etc. These proteins serve as a protective reservoir for the bifunctional molecule and drug component thereof, thereby extending the half-life of the drug. Representative intracellular proteins for which the modulating moiety may serve as a ligand in this embodiment include the peptidyl prolyl isomerases, heat shock proteins (hsp's), tubulins, and the like, where additional potential intracellular pharmacokinetic modulating proteins are described supra. Extracellular pharmacokinetic modulating proteins are also of interest, where the proteins should be long-lived proteins that impart their long half-life to the bifunctional molecule and the drug component thereof upon formation of a binary complex with the bifunctional molecule. Representative extracellular pharmacokinetic modulating proteins of interest include: albumin, α1-acid glycoprotein, and the like. In the above embodiments, the half-life the drug component of the bifunctional molecule is generally prolonged as compared to the corresponding free drug control by a factor of about 1.5, usually by a factor of about 3 and more usually by a factor of about 6.

In those embodiments where it is desired to modulate, and specifically, reduce the hepatic first-pass metabolism of a drug, the bifunctional molecule generally includes a ligand for an abundant intracellular protein, and more specifically an abundant blood cell intracellular protein, and in certain embodiments an abundant red blood cell or erythrocyte intracellular protein. The binary complex formed between the bifunctional molecule and the intracellular pharmacokinetic modulating protein should be transient, e.g. lasting on average from about 1 to 5, usually 1 to 3 minutes and in many embodiments around two minutes. While a variety of intracellular proteins are of interest, in many embodiments, peptidyl prolyl isomerases, e.g. FKBP and cyclophilin, are preferred as the pharmacokinetic modulating protein. In these embodiments, the amount of drug that is eliminated via hepatic first-pass metabolism is decreased by a factor of at least about 2, usually by at least about 5 and more usually by at least about 10.

In those embodiments where it is desired to modulate the volume of distribution of a drug, the bifunctional molecule may include a ligand for a intracellular or extracellular pharmacokinetic modulating protein. Thus, where one wishes to change the distribution of a drug so that the drug is distributed in greater amounts in the intracellular space as compared to the extracellular space, the modulating moiety of the bifunctional molecule is a ligand for an intracellular pharmacokinetic modulating protein, e.g. peptidyl prolyl isomerase, where suitable ligands are described above. Alternatively, where it is desired to enhance the amount of drug located in the extracellular space as compared to that which is present in the intracellular space, the ligand of the bifunctional molecule is a ligand for an extracellular protein, e.g. albumin, where representative ligands and extracellular pharmacokinetic modulating proteins are further described supra.

In certain embodiments, a drug is administered as a bifunctional molecule in order to reduce the degree of blood protein or serum protein, e.g. albumin, binding of the drug. By degree of serum protein binding is meant the propensity of a drug to experience an serum protein effect, i.e. to be bound by serum protein, such as albumin (or another serum protein such as $\alpha$-1 acid glycoprotein) and be rendered inactive. In this embodiments, the drugs of interest are those drugs which have a certain affinity for the serum protein, e.g. albumin, in their free drug form, where this affinity is generally at least about $10^{-3}$, usually at least about $10^{-5}$ and more usually at least about $10^{-6}$. In certain embodiments where modulation of serum protein binding effect is desired, the affinity of the modulating ligand for the serum protein will be greater than the affinity of the drug moiety for the serum protein, usually at least about 2 fold greater, in certain embodiments at least about 3 fold greater and in other embodiments at least about 5 fold greater. The linker moiety of the bifunctional molecule is chosen such that the drug moiety of the bifunctional is displayed in manner that retains its desired activity, e.g. target binding activity, when a binary complex is formed with the serum protein, e.g. albumin. In addition, the linker is chosen such that the drug moiety cannot bind to a second serum protein, e.g. albumin molecule, to produce a tripartite complex of two serum portein molecules and a bifunctional molecule. In these embodiments, the degree of albumin binding of the drug or albumin binding effect is reduced by a factor of about 2, usually by a factor of about 3 and more usually by a factor of about 4. As such, the amount of drug that must be administered in order to be effective is generally at least about 2 fold less, in certain embodiments at least about 3 fold less and in other embodiments at least about 4 fold less than the amount of corresponding free drug that must be administered.

Methods of Use, Pharmaceutical Preparations and Kits

The subject bifunctional molecules find use in the pharmacological treatment of a host condition, e.g. a disease condition. In the methods of the subject invention, an effective amount of the bifunctional molecule is administered to the host, where "effective amount" means a dosage sufficient to produce the desired result, e.g. an improvement in a disease condition or the symptoms associated therewith. In many embodiments, the amount of drug in the form of the bifunctional molecule that need be administered to the host in order to be an effective amount will vary from that which must be administered in free drug form, where by free drug is meant drug that is not conjugated with another moiety, e.g. as is found in the subject bifunctional molecules. The difference in amounts may vary, and in many embodiments may range from 2 fold to 10 fold. In certain embodiments, e.g. where the resultant modulated pharmacokinetic property(s) results in enhanced activity as compared to the free drug control, the amount of drug that need be administered to be an effective amount is less than the amount of corresponding free drug that needs to be administered, where the amount may be 2-fold, usually about 4-fold and more usually about 10-fold less than the amount of free drug that is administered.

The bifunctional molecule may be administered to the host using any convenient means capable of producing the desired result. Thus, the bifunctional molecule can be incorporated into a variety of formulations for therapeutic administration. More particularly, the bifunctional molecule of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the bifunctional molecule can be achieved in various ways, including oral, buccal, rectal, parenteral, intraperitoneal, intradermal, transdermal, intracheal, etc., administration. In pharmaceutical dosage forms, the bifunctional molecule may be administered alone or in combination with other pharmaceutically active compounds. The following methods and excipients are merely exemplary and are in no way limiting.

For oral preparations, the bifunctional molecules can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The bifunctional molecules can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The bifunctional molecules can be utilized in aerosol formulation to be administered via inhalation. The compounds of the present invention can be formulated into pressurized acceptable propellants such as dichlorodifluoromethane, propane, nitrogen and the like.

Furthermore, the bifunctional molecules can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions. In certain embodiments, of particular interest is the use of the subject methods in disease conditions where an active agent or drug having desired activity has been previously identified, but which active agent or drug does not bind to its target with desired affinity and/or specificity. With such active agents or drugs, the subject methods can be used to enhance the binding affinity and/or specificity of the agent for its target.

The specific disease conditions treatable by with the subject bifunctional compounds are as varied as the types of drug moieties that can be present in the bifunctional molecule. Thus, disease conditions include cellular proliferative diseases, such as neoplastic diseases, autoimmune diseases, cardiovascular diseases, hormonal abnormality diseases, infectious diseases, and the like.

By treatment is meant at least an amelioration of the symptoms associated with the disease condition afflicting the host, where amelioration is used in a broad sense to refer to at least a reduction in the magnitude of a parameter, e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the bifunctional molecule, usually in oral or injectable doses and often in a storage stable formulation, are provided. In such kits, in addition to the containers containing the unit doses will be an informational package insert describing the use and attendant benefits of the drugs in treating pathological condition of interest. Preferred compounds and unit doses are those described herein above.

The following examples are offered by way of illustration and not by way of limitation.

EXPERIMENTAL

I. Modulating Half-Life

A. Introduction

The liver and kidney are the two organs where most of the biotransformation and secretion of drug molecules takes place. Both organs can take up free drug molecules but the uptake of protein-bound drug is much reduced. Therefore, drugs, that cannot associate with intracellular proteins and other molecules like lipids or which cannot bind plasma proteins, are more likely to be metabolized and excreted quickly. As a result, such molecules tend to have a short half-life.

FK506 and rapamycin are two molecules that display a long half-life, 30 hours, and 60 hours, respectively. This relatively long half-life is surprising since the molecular weights of FK506 (800 D) and rapamycin (900 D) are high relative to most drugs, and large molecular weights usually lead to rapid metabolic modification, inactivation, and excretion. The basis for the extended half-life of these two molecules is the fact that both bind with high affinity to a very abundant intracellular protein, called FKBP. There are about one million FKBP molecules in every cell of the human body. When FK506 and rapamycin enter human cells, they are retained by this large pool of FKBP. This underlying mechanism for the extension of a molecule's half-life can be used to prolong the half-lives of drugs of interest.

B. Extension of Drug Half-Life

Intracellularly acting drugs with an unsatisfactory half-life are covalently linked to ligands of FKBP. When the resulting bifunctional molecule enters a cell, it will be bound by the large FKBP pool via its FKBP ligand. For example, AG 337 is a thymidylate synthase inhibitor which is undergoing clinical trials as an anti-cancer agent. Its half-life is 2–3 hours which requires a 24 hour continuous IV infusion to achieve the desired therapeutic concentration. By coupling AG 337 to a ligand for FKBP, the drug is bound and retained by the FKBP pool inside of cells so that the half-life is of the drug is extended. As a result, the administration of the drug may be reduced to a shorter time period or may be administered using the oral route.

There are natural FKBP ligands like FK506 and rapamycin as well as many synthetic FKBP ligands. They all have somewhat different affinities for FKBP which will determine to what degree the molecule is retained and, therefore, to what extent the half-life of the drug of interest will be prolonged: Creating a series of bifunctional molecules using different FKBP ligands can allow the selection of a molecule that displays the desired pharmacokinetic properties.

The extension of half-lives of intracellularly acting drugs is not restricted to the use of ligands for FKBP. Other abundant and widely expressed proteins are cyclophilin, tubulin, actin or the heat shock proteins (hsp's). Cyclophilin has high affinity ligands called cylosporins. Tubulin's high affinity ligands are molecules like nocodazole, vinblastine and colchicine, whereas cytochalasins and latrunculins are ligands for actin. Geldanamycin is a high affinity ligand for the abundant hsp90. Like FKBP ligands, the listed ligands are coupled to drugs of interest in order to change their half-lives. One important aspect in the choice of ligand is its expected toxicity at the concentrations one anticipates to use. In this respect, FKBP and cyclophilin ligands are of great interest because they display little toxicity even at high concentrations if they are derivatized so that they cannot inhibit the drug targets of FK506, rapamycin or cyclosporin A.

Two important drug binding molecules in plasma are albumin and α1 acid glycoprotein. Albumin has two binding sites for small molecule ligands. Site I shows a preference for heterocyclic compounds with a negative charge and site II seems to prefer small aromatic carboxylic acids. In addition to small molecule binding sites, albumin also has binding sites for lipids. α1 acid glycoprotein has only one binding site for small molecules. In contrast to albumin, α1 acid glycoprotein binds neutral or basic small molecules like propanolol, chlorpromazine, dipyrimadole, metoclopramide, aprindine or verapamil.

In order to prolong the half-lives of drugs, bifunctional molecules are synthesized which contain an albumin binding ligand or an α1 acid glycoprotein ligand covalently linked to the drug of interest. For example, naproxen is a small molecule that shows extensive binding to albumin. The half-life of naproxen is 14 hours. By linking it to a drug like lidocaine, which has a half life of only two hours, one can extend the half life of lidocaine.

Another albumin ligand of interest is warfarin. In plasma, warfarin is almost completely bound by albumin and it has a half-life of 25–60 hours. The volume of distribution of warfarin is equivalent to the space that albumin can reach. These properties make warfarin a good ligand to link to a drug of interest that has an extracellular target and whose half-life needs to be prolonged. Aside from various candidate small molecule drugs, such drugs can be peptides. Many peptides are agonists or antagonists for extracellular receptors like opiate peptides (e.g. enkaphalins and endorphins), orexins, leptin, insulin, vasopressin, growth hormone, erythropoietin, cytokines, renin and thrombin inhibitors and many more. In general, peptide drugs have very short half-lives because the free peptide is rapidly cleared by the liver. Coupling peptide drugs to warfarin will lead to bifunctional molecules that are avidly bound by albumin. Due to the binding to albumin, the rate of clearance of the peptide is much reduced and the half-life is prolonged.

There are many well characterized albumin ligands that can be used to extend the half-life of drugs by making bifunctional molecules. However, additional albumin ligands with potentially higher affinity than above mentioned ligands can be found by screening small molecule libraries. Every chosen albumin ligand may have different properties with respect to the half-life and the volume of distribution it confers onto the bifunctional molecule. Hence, if various ligands with different albumin binding properties are used in combination with one drug of interest, a series of bifunctional molecules can be produced with different pharmacokinetic properties for distinct therapeutic requirements.

II. Hepatic First-Pass Metabolism

Many drugs experience extensive metabolism during their first pass through the liver. In order to avoid hepatic first-pass clearance, the drug of interest is covalently linked to an FKBP ligand like FK506 or rapamycin. FKBP is highly expressed in red blood cells. After the uptake from the gut, the bifunctional molecule can diffuse into red blood cells where it is retained by binding to the large FKBP pool. In contrast to the free drug, which is accessible by endothelial cells in the liver, the bifunctional molecule can pass the liver inside red blood cells. As a result, the drug of interest is not taken up by the liver where it would be metabolized or excreted into the bile. The interaction between FKBP and the bifunctional molecule is transient. The bifunctional molecule will diffuse out of red blood cells in less than two minutes. It will then enter the next red blood cell or a tissue cell. Drugs that show extensive hepatic first-pass clearance are mercaptopurine, naloxone, verapamil, nifedipine, diltiazem, lovastatin, simvastatin, pravastatin, fluorostatin, propanolol, or propafenone.

III. Volume of Distribution

One important characteristic of a drug is its volume of distribution which reflects its distribution and degree of retention in tissues throughout the body. Highly lipophilic drugs like many dihydrofolate reductase inhibitors (e.g. piritrexim, trimetrexate) and thymidylate synthase inhibitors (e.g. AG331, AG337) often pass quickly through cells without reaching the therapeutic concentration required in the cytoplasm. To improve the distribution of such molecules and to improve their retention in the cytoplasm of cells, they are linked to FKBP ligands to form bifunctional molecules. All cells in the human body express high levels of FKBP. Bifunctional molecules that are based on FKBP ligands are slowed down in their passage through tissues and show a good volume of distribution like the drugs FK506 and rapamycin do. These drugs are found in all tissues despite the fact that they are quite lipophilic.

Similarly, drugs directed against extracellular targets should not enter into cells since this would reduce their effective concentration. The ideal volume of distribution of these drugs would equal the volume accessible by extracellular fluids. Sulfisoxazole and warfarin are two molecules which are found almost exclusively in the extracellular space because they are extensively bound to albumin which is found in all extracellular fluids. If a drug of interest, which tends to have a large volume of distribution, is bound to sulfisoxazole or warfarin, it will be preferentially retained in the extracellular space. Its volume of distribution will be reduced.

IV. Excessive Albumin Binding

Albumin is a very abundant plasma protein that binds many small molecules in two distinct binding pockets. For example, the non-steroidal anti-inflammatory drug ibuprofen has a Kd of $4.0 \times 10^{-7}$ M for one binding pocket and the Kd for the second binding pocket is $5.0 \times 10^{-5}$ M. Another albumin ligand is salicylic acid which is the core molecule of many analgesic-antipyretic and antiinflammatory agents. Its affinity for albumin's first binding pocket is $5 \times 10^{-6}$M and it binds the second binding pocket with an affinity of $6 \times 10^{-4}$M.

When small molecule drugs are bound by albumin they are not accessible for their drug targets. Sometimes drugs bind albumin so well that large doses of the drug have to be used in order to saturate albumin binding sites and to create a pool of free drug. For example, chlorpromazine is an antipsychotic drug that acts at dopaminergic synapses. Chlorpromazine is extensively bound to albumin and its affinity for albumin is $5 \times 10^{-6}$M. If chlorpromazine is linked to a ligand that has an affinity for albumin which is higher than chlorpromazine's affinity for albumin like ibuprofen($4 \times 10^{-7}$M), then, the bifunctional molecule will be bound by albumin through its ibuprofen moiety so that chlorpromazine sticks out of the albumin surface. Being presented at the albumin surface will allow chlorpromazine to interact with its target at the synapse. Administering chlorpromazine as a bifunctional molecule makes it possible to achieve a much higher concentration of target accessible drug in the plasma. Therefore, the amount of administered bifunctional drug can be sharply reduced with respect to free drug so that general and liver toxicities can be reduced and the efficacy of the drug can be enhanced. Good efficacy of a drug is especially important if the drug of interest is to be administered transdermally. The skin has only a limited capacity to absorb drugs so that molecules with high potency and efficacy are required for this route of drug administration. The linker connecting a ligand for a plasma protein like albumin and a drug of interest has to be designed in such a way that the drug target can still bind the drug of interest. However, the linker should position the drug of interest with respect to the protein surface so that a second albumin molecule cannot bind.

It is evident from the above results and discussion that the subject invention provides a powerful tool for improving drug efficacy by modulating one or more pharmacokinetic properties of the drug. Specifically, the subject invention provides a convenient way to modulate the pharmacokinetic properties of a small molecule drug while retaining the small molecule nature of the drug. As such, the subject method provides for the improvement of drugs currently in use. Furthermore, the subject methods can be used to improve drugs that have, until now, been clinically useless due to certain factors, e.g. short half-life, unacceptable volume of distribution, etc. Therefore, the invention provides for the potential usefulness of the variety of previously discovered and discarded biologically active compounds. Accordingly, the invention provides an important advancement in pharmacological science.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for modulating at least one pharmacokinetic property of a drug upon administration to a host, said method comprising:
    administering to said host an effective amount of a bifunctional molecule of less than about 5000 daltons consisting of said drug or an active derivative thereof and a pharmacokinetic modulating moiety, wherein said pharmacokinetic modulating moiety binds to an intracellular protein and said bifunctional molecule has at least one modulated pharmacokinetic property upon administration to said host as compared to a free drug control that comprises said drug;
    whereby at least one pharmacokinetic property of said drug upon administration to said host is modulated as compared to the free drug control.

2. The method according to claim 1, wherein said pharmacokinetic property is selected from the group consisting of half-life, hepatic first-pass metabolism, volume of distribution and degree of blood protein binding.

3. The method according to claim 1, wherein said drug targets a protein.

4. The method according to claim 1, wherein said bifunctional molecule is administered as a pharmaceutical preparation.

5. A method for modulating the half life of a drug upon administration to a host, said method comprising:
    administering to said host an effective amount of a bifunctional molecule of less than about 5000 daltons consisting of said drug or an active derivative thereof and a half-life modulating moiety, wherein said half-life modulating moiety binds to an intracellular protein and said bifunctional molecule has a modified half-life upon administration to said host as compared to a free drug control that comprises said drug;
    whereby the half life of said drug upon administration to said host is modulated as compared to the free drug control.

6. The method according to claim 5, wherein said drug targets a protein.

7. The method according to claim 5, wherein said bifunctional molecule is administered as a pharmaceutical preparation.

8. A method for modulating the hepatic first-pass metabolism of a drug upon administration to a host, said method comprising:
    administering to said host an effective amount of a bifunctional molecule of less than about 5000 daltons consisting of said drug, or an active derivative thereof and a hepatic first-pass metabolism modulating moiety, wherein said hepatic first-pass metabolism modulating moiety binds to an intracellular protein and said bifunctional molecule has a modified hepatic first-pass metabolism upon administration to said host as compared to a free drug control that comprises said drug;
    whereby the hepatic first-pass metabolism of said drug upon administration to said host is modulated as compared to the free drug control.

9. The method according to clam 8, wherein said drug targets a protein.

10. The method according to claim 8, wherein said bifunctional molecule is administered as a pharmaceutical preparation.

11. A method for modulating at least one pharmacokinetic property of a drug upon administration to a host, said method comprising:
    administering to said host an effective amount of a bifunctional molecule of less than about 5000 daltons consisting of said drug or an active derivative thereof and a pharmacokinetic modulating moiety joined by a linking group, wherein said pharmacokinetic modulating moiety binds to an intracellular protein and said bifunctional molecule has at least one modulated pharmacokinetic property upon administration to said host as compared to a free drug control that comprises;
    whereby at least one pharmacokinetic property of said drug upon administration to said host is modulated as compared to the free drug control.

12. The method according to claim 11, wherein said pharmacokinetic property is selected from the group consisting of half-life, hepatic first-pass pass metabolism, volume of distribution and degree of blood protein binding.

13. The method according to claim 11, wherein said drug targets a protein.

14. The method according to claim 11, wherein said bifunctional molecule is administered as a pharmaceutical preparation.

15. A method for modulating the half life of a drug upon administration to a host, said method comprising:
    administering to said host an effective amount of a bifunctional molecule of less than about 5000 daltons consisting of said drug or an active derivative thereof and a half-life modulating moiety joined by a linking group, wherein said half-life modulating moiety binds to an intracellular protein and said bifunctional molecule has a modified half-life upon administration to said host as compared to a free drug control that comprises said drug;
    whereby the half life of said drug upon administration to said host is modulated as compared to the free drug control.

16. The method according to claim 15, wherein said drug targets a protein.

17. The method according to claim 15, wherein said bifunctional molecule is administered as a pharmaceutical preparation.

18. A method for modulating the hepatic first-pass metabolism of a drug upon administration to a host, said method comprising:

administering to said host an effective amount of a bifunctional molecule of less than about 5000 daltons consisting of said drug or an active derivative thereof and a hepatic first-pass metabolism modulating moiety joined by a linking group, wherein said hepatic first-pass metabolism modulating moiety binds to an intracellular protein and said bifunctional molecule has a modified hepatic first-pass metabolism upon administration to said host as compared to a free drug control that comprises said drug;

whereby the hepatic first-pass metabolism of said drug upon administration said host is modulated as compared to the free drug control.

19. The method according to claim 18, wherein said drug targets a protein.

20. The method according to claim 18, wherein said bifunctional molecule is administered as a pharmaceutical preparation.

* * * * *

UNITED STATES PATENT AND TRADEMARK OFFICE
CERTIFICATE OF CORRECTION

PATENT NO. : 6,887,842 B1
APPLICATION NO. : 09/716841
DATED : May 3, 2005
INVENTOR(S) : Roger Briesewitz Page 1 of 1

It is certified that error appears in the above-identified patent and that said Letters Patent is hereby corrected as shown below:

- In column 1 line 14: Please delete the header "Acknowledgement" and paragraph beginning with "This invention" to and ending "in this invention."

Signed and Sealed this
Tenth Day of January, 2012

David J. Kappos
*Director of the United States Patent and Trademark Office*